US005828759A

United States Patent [19]

Everingham

[11] Patent Number: 5,828,759

[45] Date of Patent: *Oct. 27, 1998

[54] SYSTEM AND METHOD FOR REDUCING ENGINE NOISE

[75] Inventor: Gary Everingham, Chatham, Canada

[73] Assignee: Siemens Electric Limited, Chatam, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 565,738

[22] Filed: Nov. 30, 1995

[51] Int. Cl.[6] .......... H03B 29/00; A61F 11/06

[52] U.S. Cl. .......... 381/71.5; 381/71.7; 381/86; 181/206; 181/224

[58] Field of Search .......... 381/71, 94, 123, 381/124; 181/222, 198, 202, 206, 224, 228, 229, 282, 255; 415/119

[56] References Cited

U.S. PATENT DOCUMENTS

| | | | |
|---|---|---|---|
| 3,936,606 | 2/1976 | Wanke | 181/206 |
| 4,410,065 | 10/1983 | Harvey | 181/222 |
| 4,665,549 | 5/1987 | Eriksson et al. | 181/222 |
| 4,876,722 | 10/1989 | Dekker et al. | 381/71 |
| 5,170,019 | 12/1992 | Loe | 181/222 |
| 5,176,114 | 1/1993 | Brackett | 181/206 |
| 5,229,556 | 7/1993 | Geddes | 181/206 |
| 5,319,165 | 6/1994 | Geddes | 181/206 |
| 5,336,856 | 8/1994 | Krider et al. | 181/206 |
| 5,426,703 | 6/1995 | Hamabe et al. | 381/71 |
| 5,426,705 | 6/1995 | Yokota et al. | 381/71 |
| 5,432,857 | 7/1995 | Geddes | 381/71 |
| 5,446,790 | 8/1995 | Tanaka et al. | 381/71 |
| 5,452,577 | 9/1995 | Langer | 181/252 |
| 5,457,749 | 10/1995 | Cain et al. | 381/71 |
| 5,466,899 | 11/1995 | Geisenberger | 381/71 |
| 5,471,537 | 11/1995 | Castwell | 181/224 |
| 5,513,266 | 4/1996 | Zuroski | 415/119 |
| 5,541,373 | 7/1996 | Cheng | 381/71 |
| 5,550,334 | 8/1996 | Langley | 381/71 |
| 5,677,958 | 10/1997 | Lehringer | 181/206 |
| 5,693,918 | 12/1997 | Bremigan et al. | 381/71.5 |
| 5,703,337 | 12/1997 | Geisenberger | 181/206 |

FOREIGN PATENT DOCUMENTS

| | | | |
|---|---|---|---|
| 5098928 | 4/1993 | Japan | 181/206 |
| 5134684 | 5/1993 | Japan | 181/206 |
| 6-101444 | 4/1994 | Japan | 181/228 |

*Primary Examiner*—Curtis A. Kuntz
*Assistant Examiner*—Xu Mei

[57] ABSTRACT

A system and method for reducing noise from an internal combustion engine using a duct housing receiving induction air flow to the engine. A space is defined within the duct housing surrounding a speaker enclosure associated with a speaker facing an open space upstream of the annular space. A sound transducer at the axial location where the annular space opens into the open space generates electrical signals corresponding to engine noise propagating through the air induction ducting. The signals are amplified and phase shifted driving the speaker to output cancelling noises or sounds so as to at least reduce engine noise from the annular space. The speaker enclosure length is set to enhance speaker performance in selected frequency bands of engine noise.

9 Claims, 2 Drawing Sheets

SYSTEM AND METHOD FOR REDUCING ENGINE NOISE

BACKGROUND OF THE INVENTION

The present invention concerns reducing internal combustion engine noise in automotive vehicles.

Reducing engine noise has long been an objective of automotive designers. One approach for reducing noise or certain sounds has involved electronically generating cancelling noises in response to particular sensed engine noises to reduce such noise levels. U.S. Pat. No. 5,426,703 issued on Jun. 20, 1995 for an "Active Noise Eliminating System" and U.S. Pat. No. 5,426,705 issued on Jun. 20, 1995 for a "Vehicle Internal Noise Reduction System" relates to such systems.

Some systems have used speakers to direct certain sounds into an enclosed space such as the passenger compartment of an automotive vehicle. However, the sounds are dispersed in the space such that the cancelling sounds are less effective at reducing certain noises or sounds than if the cancelling noises or sounds are concentrated to better neutralize the noise.

The performance of such systems, however, depends on the generated cancelling noise.

It is therefore an object of the present invention to provide an active noise or sound reducing system that is more effective in reducing internal combustion engine noise.

SUMMARY OF THE INVENTION

The inventor has determined that certain internal combustion engine noises or sounds are propagated through the air induction system, and may include, for example, engine valve and combustion chamber noise, as well as the noise produced by inducing air into the engine. Accordingly, the present invention comprises an air duct housing defining an annular space receiving the air passing into the air induction system. The center of the annular space is defined by the curved perimeter of a speaker enclosure, with a speaker coaxially mounted therein, facing upstream towards the flow direction of the incoming inducted air.

A sound transducer such as a microphone is mounted to the speaker so that it is adjacent to the annular space and approximately within the speaker face plane to detect engine noises or sounds in the induction system. The microphone detects the sounds and generates corresponding electrical signals that are phase shifted so as to be 180° out of phase from the engine noise signal and amplified. The amplified phase shifted signals power the speaker driver to create a cancelling noise or sound that interacts with the engine noise or sound emanating from the annular space. The cancelling sounds from the coaxially aligned speaker cone are absorbed so as to neutralize engine noise emanating from the annular space surrounding the speaker.

The rear of the speaker enclosure is preferably covered and insulated to limit cancelling sounds from propagating through the air induction system so as to lessen the effects of out-of-phase components relating to the generated cancelling sounds.

An adapter transition duct section may also be installed upstream of the speaker enclosure to allow connection to other air induction system components, such as the air cleaner, etc.

The speaker enclosure may also be tuned by adjusting its length so as to enhance the speaker's performance in cancelling dominant or selected frequencies of engine noise.

DETAILED DESCRIPTION

In the following detailed description, certain specific terminology is used for clarity purposes and for describing a particular embodiment of the system. However, the particular embodiment is not intended to be limiting and should not be so construed since other embodiments may take different forms that are within the scope of the claims.

As described above, the inventor has determined that noises and sounds propagate through air in the air induction system, which draws air into the engine.

Figure 1:
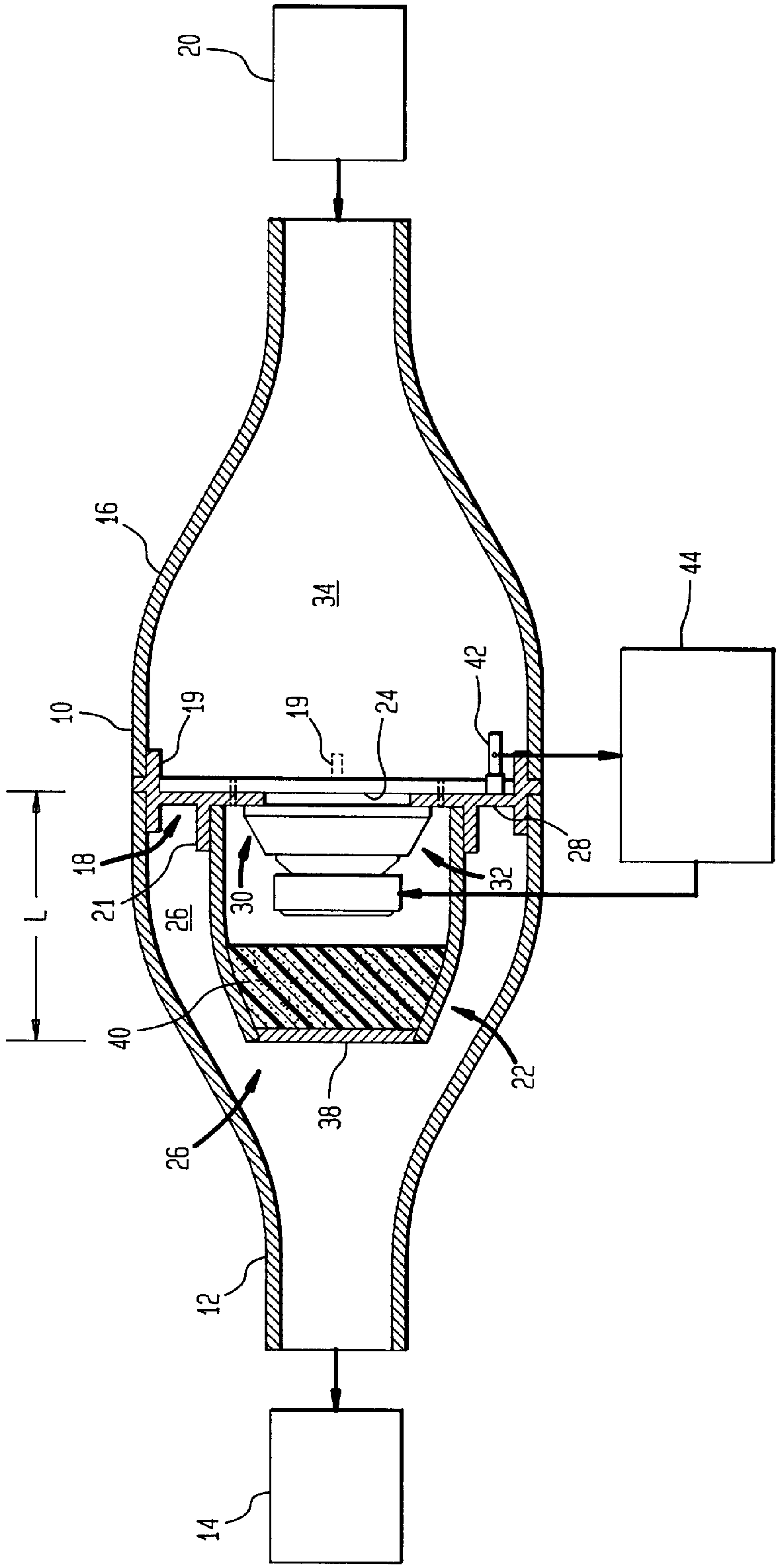
FIG. 1 shows the noise reducing system components according to the present invention together with a block diagram representation of the engine and air induction system.

As shown in FIG. 1, an air duct housing 10 is configured as a curved wall, smoothly convergent main air duct housing section 12 having a small diameter end adapted to be connected to the intake manifold of an internal combustion engine 14. An auxiliary transition section 16 may also be included, which has a divergent shape having its large end attached to or otherwise associated with a large diameter end of the main air duct housing section 12 by tabs 19 axially projecting from an outer rim 21 of a generally circular (round or oval) frame 18 attached to or otherwise associated with both structures. The transition section 16 provides convenient connection to the upstream air induction system components 20, such as the air cleaner, etc.

A speaker enclosure or assembly 22 is supported within the large end of the main air duct housing section 12 by a series of tabs 21 projecting from an inner rim 24 of frame 18. The speaker enclosure 22 has a curved outer perimeter, generally shaped to follow the inner contour of the large end of the main air duct housing section 12 so as to define a surrounding, annular air flow space 26 between the interior of the section 12 and the exterior of the enclosure 22.

The duct section 12 and speaker enclosure 22 may take various appropriate forms, including circular and oval shapes.

Figure 2:
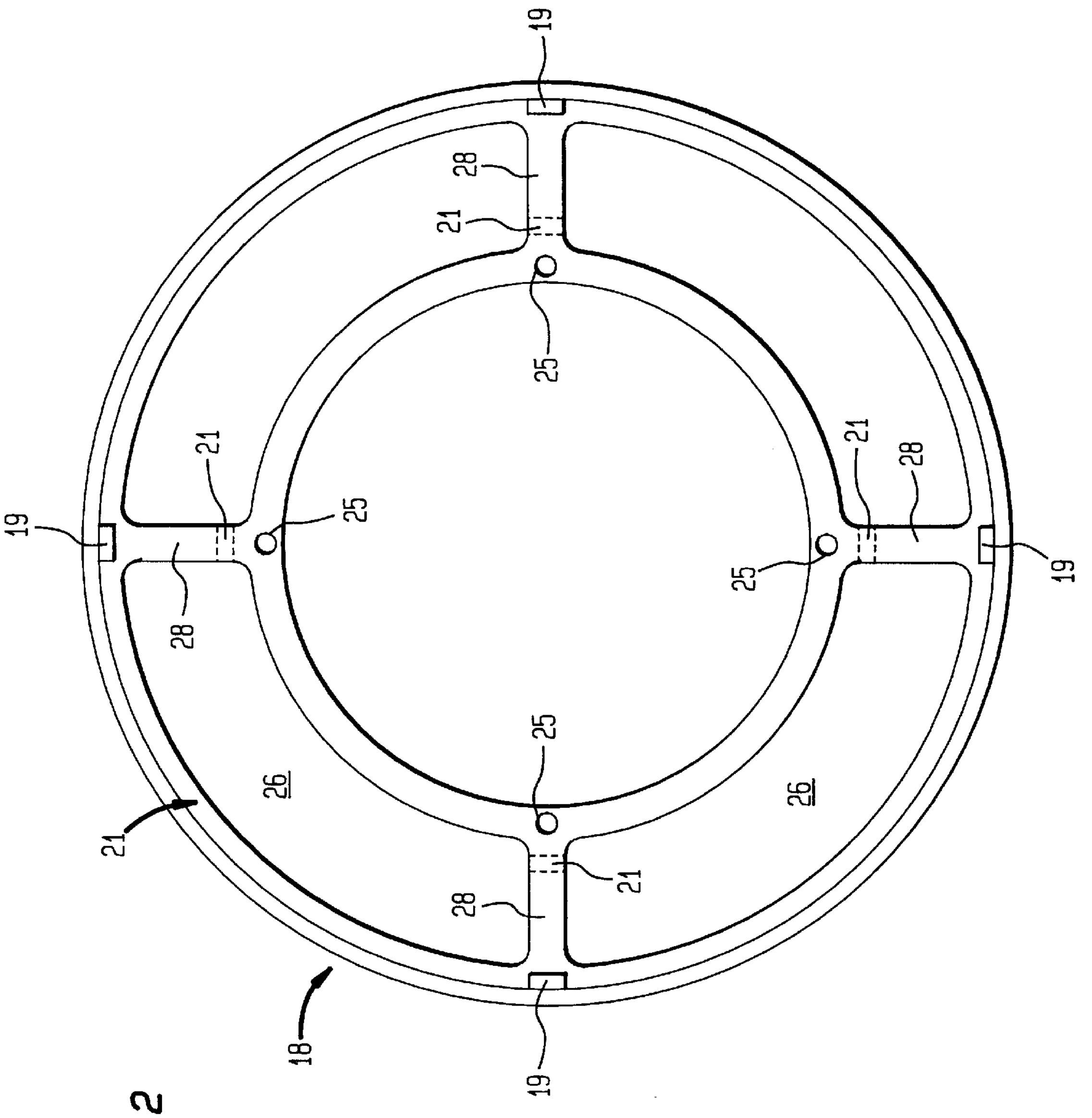
FIG. 2 is an end view of a frame component shown in section in FIG. 1.

The frame 18 shown in FIG. 2 has four equally spaced radial bars 28 supporting the inner rim 24 so as to allow adequate air flow into the annular space 26 from the transition section 16.

The speaker enclosure 22 is hollow and open at its larger diameter end facing the transition section 16, whereat the annular space 26 terminates. A speaker 30 is mounted to the rim 24 with suitable fasteners (not shown) received in holes 25 in the rim 24. The small diameter end of the speaker enclosure 22 is isolated by a solid plate 38 to reduce sounds from the rear of the speaker cone 32 that propagate to the downstream side of the speaker enclosure 22. A mass of sound deadening material 40 is disposed forward of the plate 38 and to the rear of the speaker cone 32 to further reduce such sounds.

A microphone 42 or other sound transducer is mounted within the air induction flow path by attaching it to or otherwise associating it with the frame 18 so that it is located just upstream of the annular space 26, approximately in the plane of the front of the speaker cone 32.

The microphone 42 generates an electrical signal corresponding to engine noise emanating from the annular space 26. The electrical signal is amplified in an audio broad band amplifier 44, and the amplified electrical signal is input to the driver coil of the speaker 30 to output sound from the speaker cone 32. This signal is phase shifted by 180°, such as by switching the input leads to the speaker or by electronic means (not shown), to produce an "anti noise" or cancelling sound. Since the speaker output sound is 180° out-of-phase with the engine noises or sounds, they are absorbed so as to at least partially cancel and reduce the engine noise level.

The coaxial positioning of the speaker 30 within the annular space 26 and the positioning of the microphone 42 in the approximate plane of the speaker cone 32 better reduces engine noises. Since the engine noise is confined within the annular region surrounding the speaker cone 32, the cancelling noises or sounds from the speaker are better absorbed to partially cancel engine noises or sounds so as to reduce them.

The axial length L of the speaker enclosure may be adjusted or tuned to enhance the speaker performance in selected frequency bands of the engine noises or sounds. This may be done by setting the axial length L according to the following formula:

$$L=(C/4fs)-1.9r,$$

where C is the speed of sound in air at sea level (1120 ft. per second (341.38 m/sec)), fs is the dominant or selected frequency, and r is the radius of the speaker enclosure.

I claim:

1. A system for reducing noise produced by an internal combustion engine having an air induction system for providing an air flow to supply said engine including:

a main duct for receiving all of said air flow passing through said air induction system to said engine, said main duct including a curvilinear section gradually enlarging from a small diameter portion to a substantially larger diameter portion;

said system also including a speaker enclosure positioned within said larger diameter portion of said main duct, said speaker enclosure also having a curvilinear form and said speaker enclosure coaxially positioned within said larger diameter portion of said main duct curvilinear section so as to provide an annular flow space within said main duct larger diameter portion surrounding a perimeter portion of said speaker enclosure, said air flow passing into said annular flow space;

a speaker coaxially aligned within said enclosure, said speaker having a cone facing towards the air flow into said main duct larger diameter portion, said speaker enclosure allowing sound to be projected out from one end thereof from said speaker and away from said main duct larger diameter portion;

a sound transducer assembly comprising a sound transducer positioned to generate electrical signals corresponding to engine noises propagated along said main duct;

said sound transducer assembly further comprising an audio amplifier connected to receive and amplify said electrical signals, said audio amplifier having an output operably connected to said speaker to drive said speaker with said amplified signals phase shifted by 180°, to generate cancelling sound from said speaker broadcast out from said main duct curvilinear section larger diameter portion.

2. The system according to claim 1 wherein said speaker enclosure is closed at one end and open at another end facing opposite the direction from which air flows into said main duct annual spacing, and said speaker is mounted within said enclosure facing out said open another end of said enclosure to be facing said air flow into said main duct annular space.

3. The system according to claim 2 wherein said annular flow space terminates at said open another end of said speaker enclosure.

4. The system according to claim 3 wherein said sound transducer is mounted at a point with respect to said main duct curvilinear section larger diameter portion where said annular flow space terminates, and approximately aligned with a plane at the open another end of said speaker enclosure.

5. The system according to claim 3 further including a sound absorbing material within the closed one end of said speaker enclosure.

6. A method of reducing noise generated by an internal combustion engine having an air induction system having an air duct receiving the air flow into said engine, said method comprising the steps of;

mounting a speaker coaxially within an enclosure and mounting said enclosure coaxially within a portion of said air induction system air duct defining a gradually increasing diameter curvilinear section having a small diameter portion and a large diameter portion so as to define an annular flow space within said air duct curvilinear section larger diameter portion receiving all air flow passing through said air duct and to position said speaker to project sound oppositely to the direction of air flow into said air duct annular flow space;

generating electrical signals corresponding to said engine noise at an approximate point in said air induction system air duct whereat said speaker is located;

amplifying said signals and driving said speaker with said amplified signals which are phase shifted so as to generate sound from said speaker cancelling engine noise.

7. The method according to claim 6 wherein said step of generating electrical signals corresponding to engine noise includes the step of positioning a microphone at the approximate location of said speaker in said air induction system air duct.

8. The method according to claim 6 further including the step of adjusting the axial length of said enclosure to enhance speaker performance in a dominant frequency band of said engine noise.

9. The method according to claim 8 wherein the length L of said speaker enclosure is set substantially according to the formula:

$$L=(C/4fs)-1.9r,$$

where C is the speed of sound in air, fs is the selected frequency, and r is the radius of the speaker enclosure.

* * * * *